(12) United States Patent
Yang

(10) Patent No.: US 8,686,038 B2
(45) Date of Patent: Apr. 1, 2014

(54) USE OF NITRATED LIPIDS FOR TREATMENT OF SIDE EFFECTS OF TOXIC MEDICAL THERAPIES

(75) Inventor: Tianxin Yang, Salt Lake City, UT (US)

(73) Assignee: The Univsersity of Utah Research Foundation, Salt Lake City, UT (US)

( * ) Notice: Subject to any disclaimer, the term of this patent is extended or adjusted under 35 U.S.C. 154(b) by 59 days.

(21) Appl. No.: 12/996,848

(22) PCT Filed: Jun. 18, 2009

(86) PCT No.: PCT/US2009/047825
§ 371 (c)(1),
(2), (4) Date: Mar. 4, 2011

(87) PCT Pub. No.: WO2009/155439
PCT Pub. Date: Dec. 23, 2009

(65) Prior Publication Data
US 2011/0196037 A1    Aug. 11, 2011

Related U.S. Application Data

(60) Provisional application No. 61/073,945, filed on Jun. 19, 2008.

(51) Int. Cl.
*A61K 31/201*  (2006.01)
*A61P 13/00*   (2006.01)
*A61P 13/12*   (2006.01)
*A61P 39/00*   (2006.01)

(52) U.S. Cl.
USPC ........................................................ 514/560

(58) Field of Classification Search
None
See application file for complete search history.

(56) References Cited

U.S. PATENT DOCUMENTS

| 6,407,075 B1 | 6/2002 | Scott et al. |
| 2004/0147599 A1 | 7/2004 | Gagnon et al. |
| 2007/0232579 A1 | 10/2007 | Freeman et al. |

FOREIGN PATENT DOCUMENTS

WO    WO-01/69823    2/2001

OTHER PUBLICATIONS

Park et al. Thyroid 13(12), 1103-1110 (2003).*
Schopfer et al_2005.*
Lee et al., Nephrology, Dialysis, Transplantation, 21, 2096-2105 (2006).*
Schopfer et al. in PNAS 101(32), 11577-11582 (2004).*
Cui in Journal of Biological Chemistry 281(47) 35686-35698 (2006).*
Gregory et al. in Drugs 55(2):173-189 (1998).*
'Virtual Chembook' in www.elmhurst.edu/~chm/ychembook/551fattyacids.html (retrieved from the internet Dec. 12, 2012).*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Baker et al. in PNAS 101(32), 11577-11582 (2004).*
First Office Action issued in Chinese Patent Application No. 200980127890.X and received Oct. 21, 2011. *English summary provided.*
Junping Wang et al: "Pharmacokinetics and antitumor effects of vincristine carried microemulsions composed of PEG-lipid, oleic acid, vitamin E and cholesterol", Int J Pharm, Jan. 30, 2003, vol. 251, No. 1-2, pp. 13-21, abstract provided.
Menendez J A et al, "Effects of gamma-linolenic acid and oleic acid on paclitaxel cytotoxicity in human breast cancer cells" European Journal of Cancer (Oxford, England: 1990)Feb. 2001, vol. 37, No. 3, pp. 402-413, *abstract provided.*
Supplementary European Search Report issued in European Patent Application No. 09767748.8 and dated Dec. 8, 2011.
Baker et al., "Fatty acid transduction of nitric oxide signaling," J of Bio Chem, Dec. 23, 2005, vol. 280, No. 51, pp. 42464-42475.
International Preliminary Report on Patentability for PCT/US2009/047825 dated Jan. 6, 2011.
International Search Report and Written Opinion for PCT/US09/047825 dated Mar. 5, 2010.
Li et al., "PPARalpha ligand protects during ciaplatin-induced acute renal failure by preventing inhibition of renal FAO and PDC activity," Am J Physiol Renal Physiol, 2004, vol. 286, pp. F572-F580.
Lim et al., "Nitrolinoleate, a nitric oxide-derived mediator of cell function: Synthesis, characterization, and vasomotor activity," Proceedings of Nat'l Academy of Sciences USA, Dec. 10, 2002, vol. 99, No. 25, pp. 15941-15946.
Liu et al., "Nitro-oleic acid protect the mouse kidney from ischemia and reperfusion injury," Am J Physiol Renal Physiol, 2008, vol. 295, pp. F942-F949.
Schopfer, et al., "Nitrolinoleic acid: An endogenous peroxisome proliferator-activated receptor gamma ligand," Proceedings of Nat'l. Academy of Sciences USA, Feb. 15, 2005, vol. 102, No. 7, pp. 2340-2345.
EP Communication issued on European Patent Application No. 09767748.8 dated Dec. 27, 2011.

* cited by examiner

*Primary Examiner* — Dennis Heyer
(74) *Attorney, Agent, or Firm* — David G. Rosenbaum; Eric J. Choi; Rosenbaum IP

(57) ABSTRACT

The present invention relates to methods of treating the side effects of a toxic medical therapy using nitrated lipids. In particular, the methods comprise the use of nitrated fatty acids or esters thereof to treat side effects, including organ system damage, caused by chemotherapy, radiotherapy, and the administration of other toxic agents.

5 Claims, 6 Drawing Sheets

USE OF NITRATED LIPIDS FOR TREATMENT OF SIDE EFFECTS OF TOXIC MEDICAL THERAPIES

This application is a National Stage Entry of International Application PCT/US2009/047825, International Filing Date Jun. 18, 2009, which claims priority from U.S. Provisional Application No. 61/073,945, filed Jun. 19, 2008.

CROSS-REFERENCE TO RELATED APPLICATIONS

The present application is a U.S. national stage application claiming the benefit of International Application No. PCT/US2009/047825, filed on Jun. 18, 2009, which claims the benefit of U.S. Provisional Application No. 61/073,945, filed on Jun. 19, 2008, the entire contents of which are incorporated herein by reference in their entireties.

STATEMENT OF GOVERNMENT RIGHTS

This invention was made with government support under RO-1 HL079453 and RO-1 DK 066592 by the National Institutes of Health. The government has certain rights to this invention.

FIELD OF THE INVENTION

The present invention relates to methods of treating the side effects of a toxic medical therapy using nitrated lipids. In particular, the methods comprise the use of nitrated fatty acids or esters thereof to treat side effects, including organ system damage, caused by chemotherapy, radiotherapy, and the administration of other toxic agents.

BACKGROUND OF THE INVENTION

Chemotherapy and radiotherapy provide an effective means of treating cancer. For example, cisplatin is among of the most successful anticancer drugs and is now being widely used for the treatment of testicular, head and neck, ovarian, cervical, nonsmall cell lung carcinoma, and many other types of cancer. In addition, approximately half of cancer patients received radiotherapy as a single and adjuvant therapy at some stage of their illness. However, a drawback of both chemotherapy and radiotherapy is the production of toxicity in normal tissues. For example, the clinical use of cisplatin is limited by its severe side effects, including neurotoxicity, ototoxicity, nausea and vomiting, hair loss, and nephrotoxicity. The mechanism of cisplatin-induced organ damage has been shown to be multifactorial, involving oxidative stress and apoptosis. Other kinds of medical treatment may also involve administration of toxic agents, i.e., those that produce toxicity in normal tissues. Like chemotherapy and radiotherapy, the side effects associated with such treatments may limit the use of the treatment.

SUMMARY

In one aspect, the present invention provides methods and medicaments useful in the treatment of the side effects of toxic medical therapies. The methods involve administration of at least one nitrated lipid to a subject in need thereof in amounts effective to treat a side effect of a toxic medical therapy. In some embodiments of the present methods, the side effect is reduced relative to the side effect prior to administration of the nitrated fatty acid or ester thereof. The nitrated lipids may be used to prepare medicaments for treating a side effect of a toxic medical therapy.

A variety of nitrated lipids may be used in the present methods, including, e.g., nitrated fatty acids and esters thereof. In some embodiments, the nitrated fatty acid is a monounsaturated fatty acid (e.g., oleic acid) or a polyunsaturated fatty acid. In illustrative embodiments, the oleic acid is selected from 9-nitrooleic acid, 10-nitrooleic acid, or combinations thereof.

From the methods disclosed herein, a variety of lipids may be used to form the nitrated lipids, including, but not limited to a fatty acid or an ester thereof. Similarly, a variety of fatty acids are compatible with the disclosed methods, including, but not limited to, monounsaturated and polyunsaturated fatty acids. Procedures for synthesizing nitrated lipids, sources for obtaining the lipids, and administration routes for the nitrated lipids are also provided.

Using the present methods variety of side effects may be treated, including, but not limited to organ system damage, nausea, vomiting, and hair loss. Examples of organ system damage include damage to the urinary system, the digestive system, the nervous system, the auditory system, the circulatory system, the endocrine system, the excretory system, the skeletal system, the respiratory system, the reproductive system, the muscular system, the lymphatic system, and the integumentary system. In some embodiments, the organ system is the urinary system and the urinary system damage may include damage to one or more kidneys.

Similarly, the methods encompass a variety of toxic medical therapies, including, but not limited to, chemotherapy, radiotherapy, and other therapies involving the administration of an agent that is capable of producing toxicity in normal tissues and/or non-target tissues (i.e., tissues that are not targeted for the therapeutic effect of the toxic medical therapy). toxic medical therapy comprises administration of an agent selected from the group consisting of mechlorethamine, cyclophosphamide, chlorambucil, carboplatin, oxaliplatin, cisplatin, azathioprine, mercaptopurine, vinca alkaloids, etoposide, teniposide, paclitaxel, docetaxel, irinotecan, topotecan, amsacrine, trastuzumab, cetuximab, rituximab, bevacizumab, dexamethasone, finasteride, aromatase inhibitors, tamoxifen, goserelin, antibiotics, contrast agents, NSAIDS, COX-2 inhibitors, ACE inhibitors, ARBs, and lithium. In some embodiments, the toxic medical therapy is chemotherapy comprising administration of cisplatin.

The effective amount of the nitrated lipid administered to the subject may vary. In some aspects, the effective amount is that which prevents the subject from experiencing any of the disclosed side effects with any of the disclosed toxic medical therapies. In other aspects, the effective amount is an amount that reduces or eliminates the subject's side effects relative to the subject's side effects prior to administration of the nitrated lipid.

The methods disclosed herein may further comprise administrating a variety of therapeutic agents useful in the treatment of the underlying condition, disease, or disorder giving rise to any of the toxic medical therapies disclosed herein.

DETAILED DESCRIPTION

Figure 1:
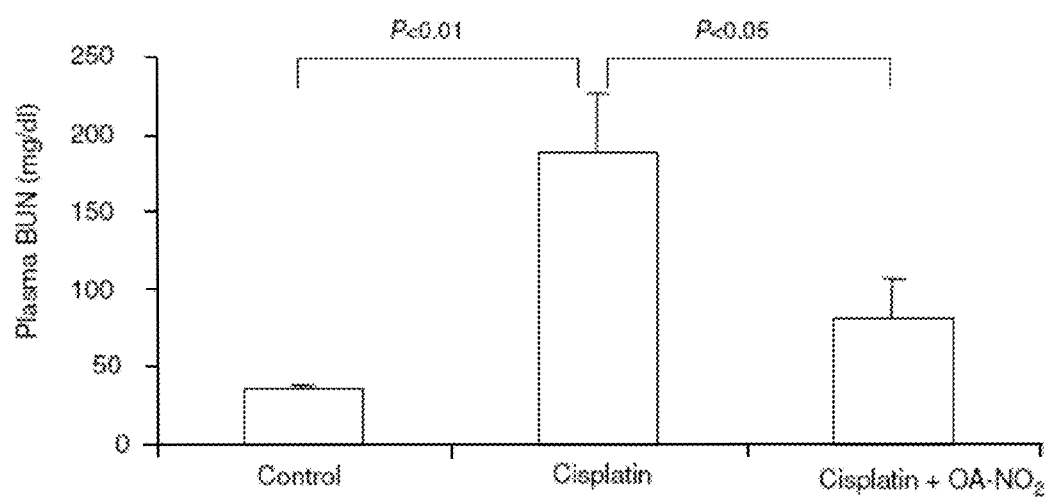
FIG. 1. Shown are plasma concentrations of BUN in mice under the conditions indicated. N=5-6. Data are mean±SE. B6129S2/J mice (male, 3-4-mo-old) received vehicle (Control) or a single i.p. injection of cisplatin alone (20 mg/kg in saline). After 20 min, the cisplatin group was randomly divided to receive an i.p injection of OA-NO2 (400 mg/kg in ethanol) or an equivalent amount of ethanol at 6-h intervals for 48 h. The results show that nitrated fatty acid OA-NO2 improves renal function in a mouse model of cisplatin-induced toxicity.

The following terms are used throughout as defined below.

"Treat" means to alleviate, in whole or in part, symptoms associated with a condition or disorder (e.g., disease), or halt of further progression or worsening of those symptoms, or prevention or prophylaxis of the condition or disorder. Similarly, as used herein, an "effective amount" of a compound disclosed herein refers to an amount of the compound that alleviates, in whole or in part, symptoms associated with a condition or disorder, or halts further progression or worsening of those symptoms, or prevents or provides prophylaxis for the disease or disorder. For example, in treating a side effect of a toxic medical treatment, the prevention of, reduction of, or elimination of the side effect are examples of desirable treatment results. Finally, treating does not necessarily occur by administration of one dose of the compound, but often occurs upon administration of a series of doses. Thus, an effective amount, an amount sufficient to alleviate, or an amount sufficient to treat a disease, disorder, or condition may be administered in one or more administrations.

The methods disclosed herein comprise administration of a nitrated lipid. Nitrated lipids are lipids comprising at least one nitro ($NO_2$) group covalently bonded to the lipid. The methods disclosed herein encompass administration of a single type of nitrated lipid or a mixture of two or more different types of nitrated lipids. By way of example, one type of nitrated lipid is 9-nitro-9-cis-octadecenoic acid. Thus, "type" identifies the compound by lipid, stereochemistry, and number and position of $NO_2$ groups.

Nitrated lipids include nitrated fatty acids or esters thereof. A fatty acid is a substituted or unsubstituted alkyl or alkenyl having a terminal COOH group. In some embodiments, the alkyl or alkenyl is a $C_8$-$C_{24}$ alkyl or alkenyl. A wide variety of fatty acids may be used, including, but not limited to monounsaturated fatty acids and polyunsaturated fatty acids. In some embodiments, the monounsaturated fatty acid is oleic acid. In some embodiments, the oleic acid is 9-nitrooleic acid, 10-nitrooleic acid, or combinations thereof. An ester of a fatty acid is a substituted or unsubstituted alkyl or alkenyl having a terminal COOR group. In some embodiments, the alkyl or alkenyl is a $C_8$-$C_{24}$ alkyl or alkenyl. R may include, but is not limited to, a $C_{1-8}$ alkyl or glyceryl.

Nitrated lipids may be synthesized according to known procedures. For example, U.S. Patent Publication No. 2007/0232579 (incorporated herein by reference in its entirety) discloses a procedure comprising the steps of reacting a lipid with a mercuric salt, a selenium compound, and a nitrating compound to produce a first intermediate and reacting the first intermediate with an oxidant. Useful mercuric salts, selenium compounds, nitrating compounds, oxidants, relative amounts of reactants, and reaction conditions are also disclosed in U.S. Patent Publication No. 2007/0232579. Such synthetic procedures may provide mixtures of two or more types of nitrated lipids which may be separated or purified by techniques known in the art, if desired.

The lipids described above may be obtained from a variety of sources. For example, lipids may be commercially available or may be obtained from natural sources. Plant oils, including, but not limited to olive oil, linseed oil, flaxseed oil, rapeseed oil, and perilla oil are possible natural sources of fatty acid lipids. Fish oils or other marine oils are other possible sources of fatty acids. Nitrated lipids present in any of these or other natural sources may be extracted and/or purified for use in the methods disclosed herein.

The disclosed methods involve treatment of a side effect of a toxic medical therapy. A variety of side effects may be treated, including, but not limited to organ system damage, nausea, vomiting, and hair loss. By organ system, it is meant a group of related organs. By way of example only, the urinary system is an organ system including the kidneys, the ureters, the bladder, and the urethra. Other examples of organ systems include, but are not limited to, the digestive system, the nervous system, the auditory system, the circulatory system, the endocrine system, the excretory system, the skeletal system, the respiratory system, the reproductive system, the muscular system, the lymphatic system, and the integumentary system. "Organ system damage" refers to damage to one or more of the organs making up the organ system as a result of a toxic medical therapy. Organ damage may include, but is not limited to, oxidative stress to the organ, and necrosis or apoptosis of organ cells.

These examples of organ damage and others may be readily identified using well-known pathological techniques. By way of example only, kidney damage may be identified by examining the overall renal morphology, the dilation of renal tubules, and the appearance of protein cast. Organ damage may also be identified by measuring certain biomarkers of organ damage in a subject. Useful biomarkers include, but are not limited to biological substances or activities that provide a marker of organ dysfunction, oxidative stress, necrosis or apoptosis. By way of example only, a biomarker of organ dysfunction includes, but is not limited to the rise of plasma creatinine and BUN for renal dysfunction, and the rise of serum aspartate aminotransferase (AST) and alanine aminotransferase (ALT) for hepatic dysfunction. Biomarkers of oxidative stress include, but are not limited to, the NADPH oxidase subunits $p47^{phox}$ and $gp91^{phox}$ and thiobarbituric acid-reactive substances (TBARS). A biomarker of apoptosis includes, but is not limited to, the activity of caspase 3, 6, and 9. Another biomarker of organ damage is myeloperoxidase, MPO. An increase in the level of MPO, BUN, AST, ALT, TBARS, $p47^{phox}$, or $gp91^{phox}$ in a subject or an increase in the activity of caspase 3, 6, and 9 in the subject may provide an indication of organ damage.

The disclosed methods encompass a variety of toxic medical therapies. By toxic medical therapy it is meant a medical therapy that involves administration of an agent that is capable of producing toxicity in normal tissues. The agent may be chemical or physical. Chemical agents include, but are not limited to, alkylating agents, anti-metabolites, alkaloids and terpenes, topoisomerase inhibitors, antibiotics, monoclonal antibodies, tyrosine kinase inhibitors, and hormones. Examples of alkylating agents include, but are not limited to, cisplatin, mechlorethamine, cyclophosphamide, chlorambucil, carboplatin, and oxaliplatin. Examples of antimetabolites include, but are not limited to azathioprine, mercaptopurine, and other purine and pyrimidine analogues. Examples of alkaloids and terpenes include, but are not limited to, vinca alkaloids, etoposide, teniposide, paclitaxel, and docetaxel. Examples of topoisomerase inhibitors include, but are not limited to, irinotecan, topotecan, and amsacrine. Examples of monoclonal antibodies include, but are not limited to, trastuzumab, cetuximab, rituximab, and bevacizumab. Examples of hormones include, but are not limited to, steroids such as dexamethasone, finasteride, aromatase inhibitors, tamoxifen, and goserelin. Other examples of chemical agents include, but are not limited to, contrast agents, NSAIDS, COX-2 inhibitors, ACE inhibitors, ARBs, and lithium. An example of a physical agent includes, but is not limited to, radiation. By way of example only, the radiation may be ionizing radiation or laser radiation.

In the disclosed methods, the nitrated lipids are administered to a subject in an effective amount. An effective amount is an amount that 1) prevents the subject from experiencing any of the disclosed side effects associated with any of the disclosed toxic medical therapies; 2) reduces the subject's side effects relative to the subject's side effects prior to administration of the nitrated lipid; and/or eliminates the subject's side effects relative to the subject's side effects prior to administration of the nitrated lipid. By way of example only, in some embodiments, the side effect is urinary system damage comprising damage to one or more kidneys. In this illustrative example, the effective amount is an amount that prevents, reduces, or eliminates the damage to the kidneys. The damage to the kidneys may include, but is not limited to, any of the types of damage described above.

As is understood by those of skill in the art, specific effective amounts of the nitrated lipids to be administered will vary depending upon a variety of factors, e.g., the condition to be treated, the age, body weight, general health, sex, and diet of the subject, the dose intervals, and the administration route. In some embodiments, the effective amount of the nitrated lipid ranges from about 1 µg per day to about 1 g per day, from about 1 mg per day to about 500 mg per day, from about 1 mg per day to about 100 mg per day, or from about 2 mg per day to about 10 mg per day.

Any of the nitrated lipids disclosed herein may be administered to the subject alone or in combination with one or more other therapeutic agents. By "administered in combination," it is meant that the nitrated lipids and the therapeutic agents may be administered as a single composition, simultaneously as separate doses, or sequentially. Sequential administration refers to administering the nitrated lipids and at least one therapeutic agent either before or after the other. A variety of therapeutic agents may be used, including, but not limited to, those useful in the treatment of the underlying condition, disease, or disorder giving rise to any of the toxic medical therapies disclosed herein.

The nitrated lipids may be administered to a subject via any number of pharmaceutical formulations and administration routes. The formulations can take the form of granules, powders, tablets, capsules, syrup, suppositories, injections, emulsions, elixirs, suspensions or solutions. These formulations may further include a variety of well-known pharmaceutically acceptable additives, carriers, and/or excipients as necessary. The formulations may be delivered to the subject by various routes of administration, e.g., by topical administration, transdermal administration, oral administration, by nasal administration, rectal administration, subcutaneous injection, intravenous injection, intramuscular injection, or intraperitoneal injection. Any of the formulations, delivery methods, and pharmaceutically acceptable additives, carriers, and excipients disclosed in U.S. Patent Publication No. 2007/0232579 may also be used with the methods described herein. Another possible route of administration includes incorporating the nitrated lipid into various food products. Food products, include, but are not limited to butter, margarine, vegetable oils, and the like.

The subjects of the disclosed methods include any animal that can benefit from the administration of a nitrated lipid. In some embodiments, the subject is a mammal, e.g., a human, a primate, a dog, a cat, a horse, a cow, a pig, or a rodent, e.g., a rat or mouse. Typically, the mammal is a human. In some aspects, the subject is undergoing or has undergone any of the disclosed toxic medical therapies. Such subjects may or may not actually be experiencing any of the disclosed side effects. In other aspects, the subject has not yet undergone the toxic medical therapy, but is susceptible to any of the disclosed side effects because of an imminent toxic medical therapy.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

For the purposes of this disclosure and unless otherwise specified, "a" or "an" means "one or more."

The present invention, thus generally described, will be understood more readily by reference to the following examples, which are provided by way of illustration and are not intended to be limiting of the present invention.

EXAMPLES

Materials and Methods

Animals.

Male 3-4-month-old B6129SF2/J mice were from Jackson Laboratories (Bar Harbor, Me.). All animals were housed in an air-conditioned room with a 12-hour light/dark cycle. All procedures and protocols were in accordance with guidelines set by the Laboratory Animal Care Committee at the University of Utah.

Materials.

9-Nitrooleic acid and 10-nitrooleic acid are two regioisomers of nitrooleic acid (OA-NO2), which are formed by nitration of oleic acid in approximately equal proportions in vivo. The two compounds were purchased from Cayman Chemicals (Ann Arbor, Mich.) (9-nitrooleic acid: Cat#10008042; 10-nitrooleic acid: Cat#10008043) and used as an 1:1 mixture of the isomers.

Protocols for Animal Experiments.

Protocol for Testing Effects of OA-NO2 on Cisplatin-Induced Toxicity in B6129SF2/J Mice.

B6129S2/J mice (male, 3-4-mo-old) received vehicle (saline) or a single i.p. (intraperitoneal) injection of cisplatin alone (20 mg/kg in saline). After 20 minutes, the cisplatin group was randomly divided to receive an i.p injection of OA-NO2 (400 mg/kg in ethanol) or an equivalent amount of ethanol at 6-hour intervals for 48 hours. The control group also received an i.p. injection of the equivalent amount of ethanol at the same frequencies. At the end of the experiments, under isoflurane anesthesia, blood was withdrawn from the vena cava using 1 cc insulin syringe and kidneys were harvested for analysis of morphology and gene expression.

Example

Figure 2:
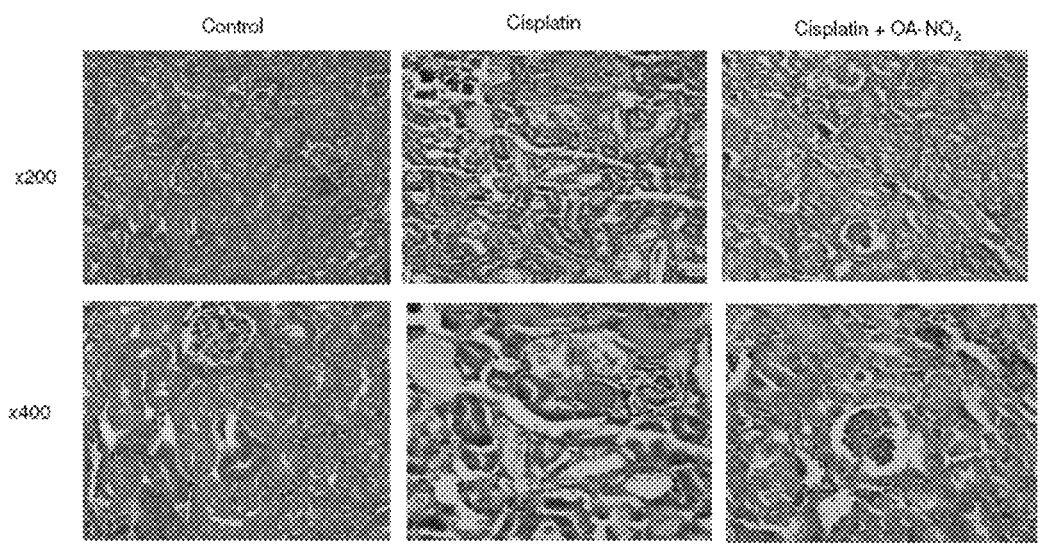
FIG. 2. The nitrated fatty acid OA-NO2 improves renal morphology in a mouse model of cisplatin-induced toxicity. Shown are representative images of renal morphology at ×200 and ×400 magnifications.
Figure 3:
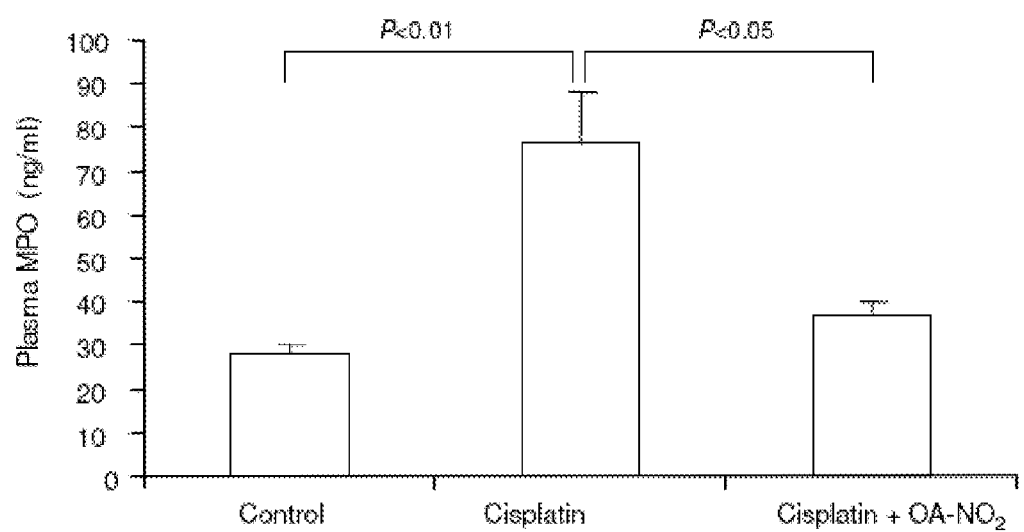
FIG. 3. The nitrated fatty acid OA-NO2 reduces plasma myeloperoxidase (MPO) in cisplatin treated mice. MPO concentrations are determined by EIA. N=5–6. Data are mean±SE.
Figure 4:
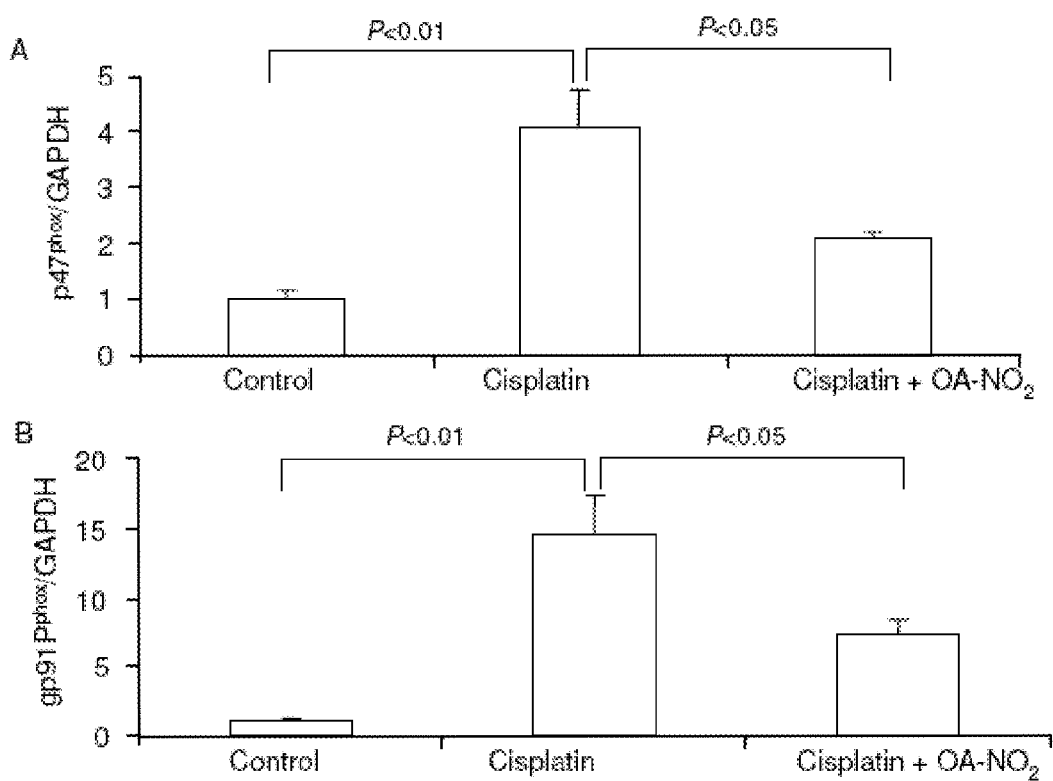
FIG. 4. Real time RT-PCR analysis of $p47^{phox}$ (A), $gp91^{phox}$ (B) in control mice and mice treated with cisplatin alone or in combination with OA-NO2. N=5–6 in each group. Data are mean±SE.
Figure 5:
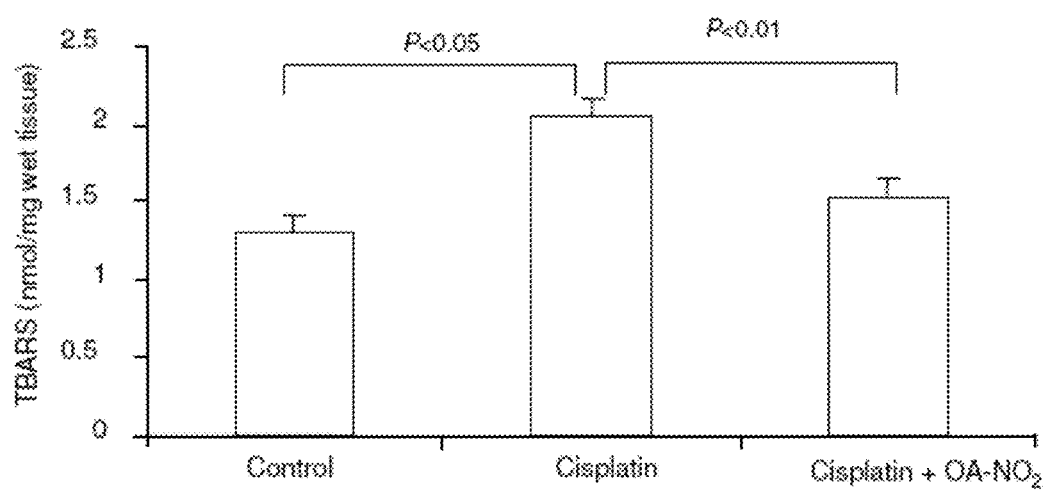
FIG. 5. Kidney TBARS in control mice and mice treated with cisplatin alone or in combination with OA-NO2. N=5–6 in each group. Data are mean±SE.
Figure 6:
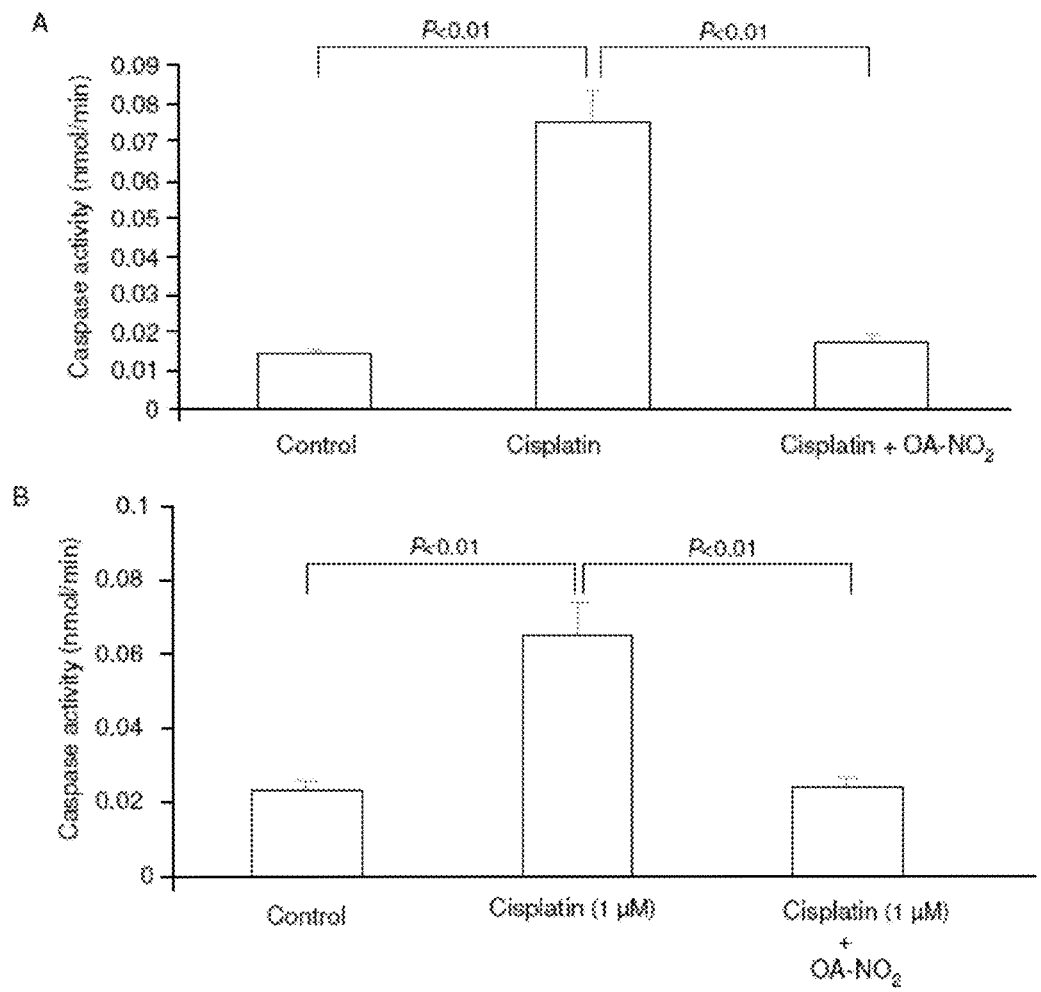
FIG. 6. Effects of nitrated fatty acid OA-NO2 on cisplatin-induced apoptosis in vivo and in vitro. A), Caspase activity in the mouse kidney. N=5-6 in each group. B), Caspase activity in cultured human proximal tubular cells (HK2). Following pretreatment for 1 h with vehicle or 1.5 µM OA-NO2, the cells were exposed for 24 h to 1 µM cisplatin. N=3 in each group. Data are mean±SE.

Evaluation of the Therapeutic Potential for Using Nitrated Fatty Acid OA-NO2 in Managing Chemotherapy-Related Toxicity A single dose of i.p. injection of cisplatin induced renal dysfunction as indicated by the marked rise in plasma BUN (FIG. 1), accompanied by severe renal histological abnormalities characterized by distortion of the overall renal morphology, dilation of renal tubules, and appearance of protein cast (FIG. 2). In a sharp contrast, posttreatment with OA-NO2 markedly attenuated these functional and pathological changes (FIGS. 1 and 2). Cisplatin treatment induced increases in plasma level of MPO (marker of neutrophil infiltration) (FIG. 3), kidney expression of NADPH oxidase subunits $p47^{phox}$ and $gp91^{phox}$ (major superoxide generating enzyme) (FIG. 4), kidney thiobarbituric acid-reactive substances (TBARS, index of oxidative stress) (FIG. 5), and activity of caspase (index of apoptosis) (FIG. 6A), all of which were attenuated or completely corrected by OA-NO2. In cultured human proximal tubular cells (HK2), exposure to 1.0 µM cisplatin induced a 3-fold increase in caspase activity that was almost completely normalized by OA-NO2 (FIG. 6B).

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method of treating a side effect in the renal system of a subject receiving a toxic medical therapy selected from the group consisting of carboplatin, oxaliplatin and cisplatin chemotherapy comprising administering a nitrated oleic acid or ester thereof to a subject in need thereof in an amount effective to treat the side effect.

2. The method of claim 1, wherein the side effect is reduced relative to the side effect prior to administration of the nitrated fatty acid or ester thereof.

3. The method of claim 1, wherein the oleic acid is selected from 9-nitrooleic acid, 10-nitrooleic acid, or combinations thereof.

4. The method of claim 1, wherein the side effect in the renal system comprises renal damage.

5. The method of claim 1, wherein the toxic medical therapy is chemotherapy comprising administration of cisplatin.

* * * * *